United States Patent
Li

(10) Patent No.: US 8,442,658 B2
(45) Date of Patent: May 14, 2013

(54) CRIMP-THROUGH CRIMP CONNECTOR FOR CONNECTING A CONDUCTOR CABLE AND AN ELECTRODE OF AN IMPLANTABLE CARDIAC ELECTROTHERAPY LEAD

(75) Inventor: Yong Li, Valencia, CA (US)

(73) Assignee: Pacesetter, Inc., Sylmar, CA (US)

(*) Notice: Subject to any disclaimer, the term of this patent is extended or adjusted under 35 U.S.C. 154(b) by 586 days.

(21) Appl. No.: 12/363,445

(22) Filed: Jan. 30, 2009

(65) Prior Publication Data

US 2010/0198326 A1    Aug. 5, 2010

(51) Int. Cl.
*A61N 1/05* (2006.01)
(52) U.S. Cl.
USPC ............................ 607/122; 439/870; 439/877
(58) Field of Classification Search .......... 607/120–132; 600/374, 375; 439/423, 870, 877, 881; 339/97, 339/276; 29/630; 174/84
See application file for complete search history.

(56) References Cited

U.S. PATENT DOCUMENTS

| | | | |
|---|---|---|---|
| 3,964,815 A * | 6/1976 | McDonough | 439/423 |
| 4,261,632 A * | 4/1981 | Narozny | 439/394 |
| 4,461,527 A * | 7/1984 | Izraeli | 439/391 |
| 5,445,535 A * | 8/1995 | Phillips et al. | 439/394 |
| 7,228,624 B2 | 6/2007 | Culp | |
| 7,364,479 B1 | 4/2008 | Deily | |
| 2005/0090885 A1 * | 4/2005 | Harris et al. | 607/116 |
| 2007/0169954 A1 | 7/2007 | Bertini et al. | |
| 2008/0033232 A1 * | 2/2008 | Catanese et al. | 600/29 |

FOREIGN PATENT DOCUMENTS

| WO | 2007087513 A2 | 8/2007 |
|---|---|---|
| WO | 2007087513 A3 | 8/2007 |

* cited by examiner

*Primary Examiner* — Kennedy Schaetzle
*Assistant Examiner* — Erica Lee

(57) ABSTRACT

An implantable cardiac electrotherapy lead is disclosed herein. The lead may include an electrode on a distal portion of the lead, a conductor extending proximally through the lead from the electrode, and a crimp connector coupling a distal end of the conductor to the electrode. The connector may include a body with an outer surface, an inner surface, proximal and distal ends, a cavity, and at least one splice opening. The inner surface defines the cavity, the proximal and distal ends respectively define proximal and distal openings leading to the cavity, and the at least one splice opening extends from the outer surface to the inner surface and is oriented generally transverse to an axis extending between the proximal and distal openings.

16 Claims, 4 Drawing Sheets

CRIMP-THROUGH CRIMP CONNECTOR FOR CONNECTING A CONDUCTOR CABLE AND AN ELECTRODE OF AN IMPLANTABLE CARDIAC ELECTROTHERAPY LEAD

FIELD OF THE INVENTION

The present invention relates to medical apparatus and methods of manufacturing such apparatus. More specifically, the present invention relates to implantable cardiac electrotherapy leads and methods of manufacturing such leads.

BACKGROUND OF THE INVENTION

Current implantable cardiac electrotherapy leads (e.g., cardiac resynchronization therapy ("CRT") leads, bradycardia leads, tachycardia leads) utilize crimp connectors to transition from conductor cables to welded joints at the electrodes or shock coils. Such transitions are excessively expensive to create for a number of reasons. First, each transition employs a relatively expensive crimp connector individually cut using a wire electrical discharge machining process.

Second, the process for creating the transition is labor intensive. To achieve adequate electrical contact between a crimp connector and the conductive core of a cable conductor, insulation must be removed from the cable conductor where the crimp connector will be crimped onto the cable conductor.

Third, difficulty associated with the process of creating the transition results in substantial scrap. Crimp connectors may be unidirectional and are often reversed when crimped onto the cable conductor, resulting in the scrapping of the crimp connector and the cable conductor. The configuration of the crimp connector requires relatively tight tolerances for fit and placement of the crimp connector relative to a shock coil when undergoing welding. Failure to satisfy the tight tolerances can result in a weak weld between the crimp connector and the shock coil, or welding can burn a hole through the connector again requiring the lead to be scrapped.

There is a need in the art for a crimp connector that reduces the costs associated with connecting a cable conductor to a lead shock coil. There is also a need in the art for a method of employing such a crimp connector in connecting a cable conductor to a lead shock coil.

SUMMARY

An implantable cardiac electrotherapy lead is disclosed herein. In one embodiment, the lead includes an electrode on a distal portion of the lead, a conductor extending proximally through the lead from the electrode, and a crimp connector coupling a distal end of the conductor to the electrode. The connector may include a body with an outer surface, an inner surface, proximal and distal ends, a cavity, and at least one splice opening. The inner surface defines the cavity, the proximal and distal ends respectively define proximal and distal openings leading to the cavity, and the at least one splice opening extends from the outer surface to the inner surface and is oriented generally transverse to an axis extending between the proximal and distal openings.

In another embodiment, an implantable cardiac electrotherapy lead includes a tubular body, an electrode on the tubular body with a termination ring, the termination ring having an arcuate inner surface and a proximal edge, a cable conductor including an end, the cable conductor having a conductive core and an insulation jacket, and a crimp connector with an inner surface defining a cavity and an arcuate outer surface, the crimp connector coupling the cable conductor to the termination ring. The arcuate outer surface of the crimp connector nests substantially continuously against the arcuate inner surface of the termination ring. The crimp connector may include a segment of pre-drawn tubing. In another embodiment, the crimp connector further includes at least one splice opening oriented substantially transverse to a longitudinal axis of the crimp connector. In another embodiment, the at least one splice opening is at least one laser cut splice opening having a sharp edge at its intersection with the inner surface of the crimp connector. In still another embodiment, in a post-crimped position, the sharp edge penetrates the insulation jacket on the cable connector providing for electrical communication between the crimp connector and the cable connector. In yet another embodiment, the outer surface of the crimp connector is fixedly attached to the proximal edge of the termination ring.

In another embodiment, a method of manufacturing an implantable cardiac electrotherapy lead includes providing an electrode on a tubular body of the lead, forming a crimp connector from a segment of a pre-drawn tubing, receiving an end of a cable conductor in a cavity of a crimp connector, and welding an outer surface of the crimp connector to an edge of the electrode. In another embodiment, the crimp connector includes at least one splice opening. In another embodiment, the at least one splice opening is a laser cut splice opening having a sharp edge at its intersection with an inner surface of the crimp connector. In still another embodiment, the method includes crimping the crimp connector causing the sharp edge of the splice opening on the crimp connector to penetrate an insulation layer of the cable conductor to place the crimp connector in electrical contact with a conductive core of the cable conductor.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

DETAILED DESCRIPTION

The following detailed description relates to the connection between cable conductors and an electrode on a medical lead. A medical lead may be used to monitor heart function and stimulate heart function. As such, a distal end of a lead may be placed within the heart and a proximal end may be connected to a controller such as a pacemaker, ICD or other type pulse generator via a lead connector end on the proximal lead end. The distal end of the lead may have a series of electrodes including a pacing electrode, a sensing electrode, and a shocking electrode or coil. Each of the electrodes may be connected via a cable/electrode connector to a respective cable conductor or respective series of cable conductors extending the length of the lead to the lead proximal end's lead connector end mechanically and electrically coupling the lead proximal end to the controller. The cable conductors may include a conductive core covered by an insulation layer or layers. As such, the connection between the connector and the cable conductor may require removing or penetrating the insulation to provide a positive electrical connection between the two. The present disclosure is directed at the cable/electrode connector used to connect cable conductors to electrodes.

In some embodiments, as disclosed below, the cable/electrode connector may be in the form of a crimp connector. The crimp connector allows for the cable conductors to pass into the connector such that the connector may then be squeezed, pressed, or otherwise caused to grasp the cable conductors, restraining them from slipping out of the crimp connector. Moreover, in order to effectively transmit electrical current, the crimp connector may either penetrate the cable conductor insulation or the insulation may be otherwise stripped prior to crimping to create a positive electrical connection. The crimp connector may in turn be welded or otherwise connected to the electrode to complete the electrical circuit.

Figure 1:
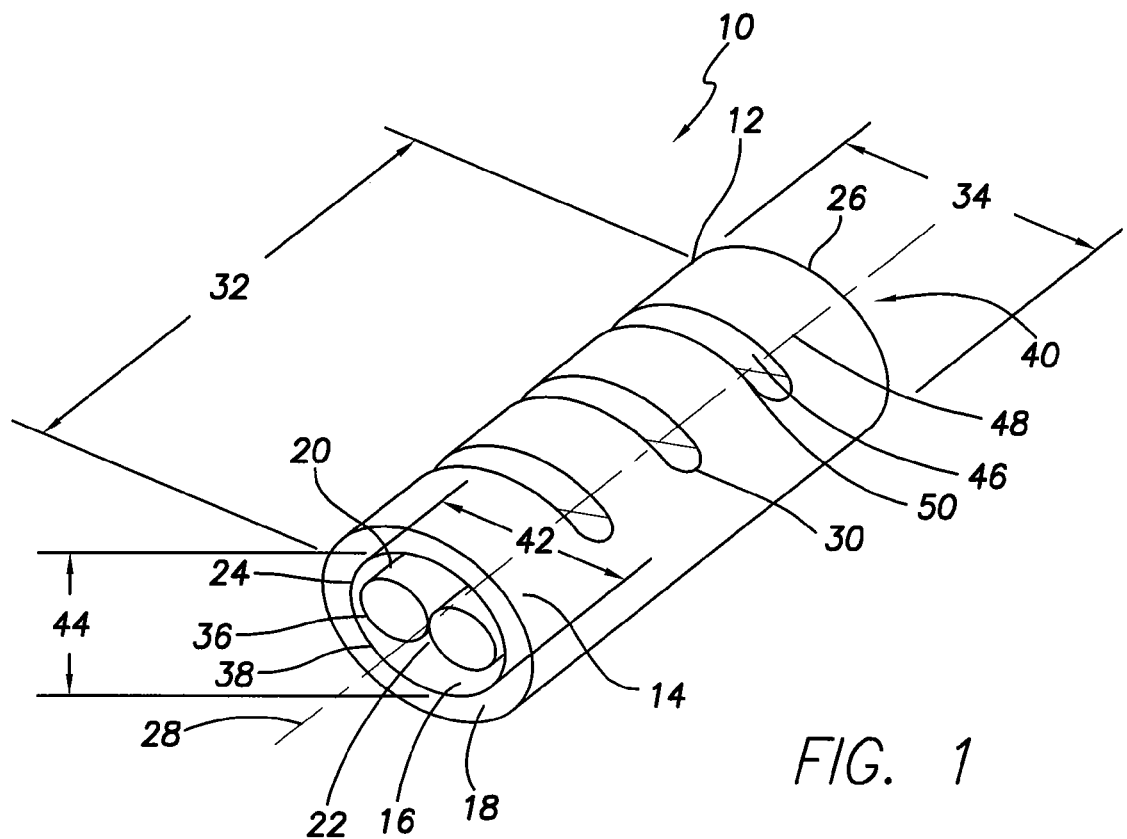
FIG. 1 is an isometric view of a crimp connector in a pre-crimp position according to certain embodiments.
Figure 2:
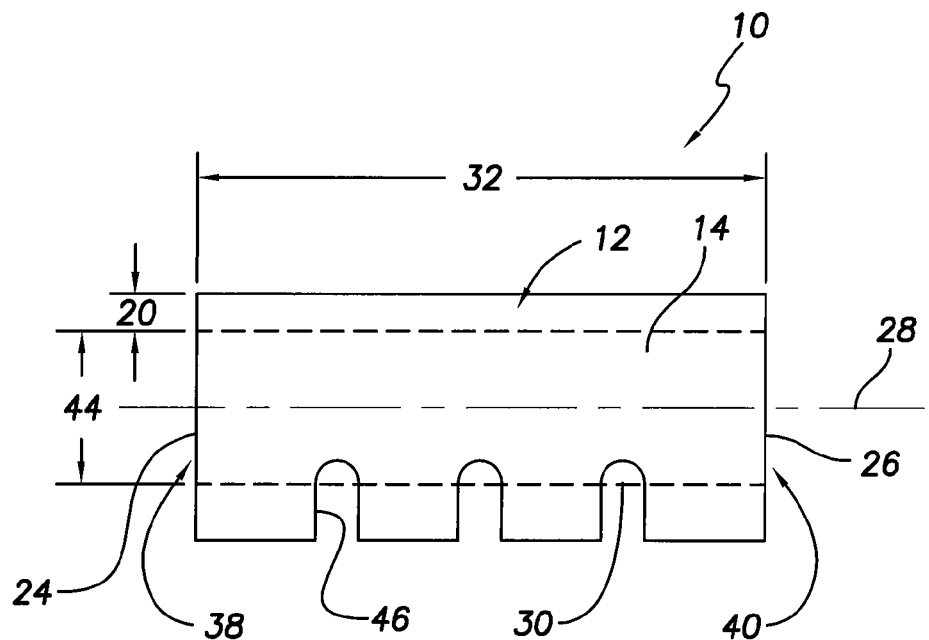
FIG. 2 is a side view of a crimp connector in a pre-crimp position according to certain embodiments.

For a discussion regarding a crimp connector 10, according to certain embodiments, reference is made to FIGS. 1 and 2. FIG. 1 is an isometric view and FIG. 2 is a side view of a crimp connector 10 in a pre-crimp position according to certain embodiments.

As can be understood from FIGS. 1 and 2, in one embodiment, the crimp connector 10 may take the form of a body 12. The body 12 may have an outer surface 14 and an inner surface 16 separated by a body wall 18 having a thickness 20 and the inner surface 16 may define a cavity 22. The body 12 may have a proximal end 24 and a distal end 26 situated along a longitudinal axis 28 of the body 12. The body 12 may also include splice openings 30 extending through the body wall 18.

As shown in FIGS. 1 and 2, in one embodiment, the body 12 may have a pre-crimp shape of a tube, the inner surface defining a generally cylindrical cavity with a round, oval, or oblong shaped cross-section. Preferably, the cross-section is oval. In this embodiment, the tube may be a segment of pre-drawn tubing. The tube may have a length 32 and a width 34, wherein the length 32 is longer than the width 34. Alternatively, the width 34 may be wider than the length 32. In the case of a cylindrical shape with a round cross-section, the width 34 may be equal to the diameter of the outer surface 14 of the tube.

As indicated in FIGS. 1 and 2, in one embodiment, the cavity 22 may be adapted to receive cable conductors 36. The proximal end 24 and distal end 26 of the body 12 may define a proximal opening 38 and a distal opening 40 respectively leading to the cavity 22 and through which the cable conductors 36 may enter the cavity 22. The cavity 22 may have a width 42 equal to the width 34 of the body 12 less the wall thickness 20 on each side of the cavity 22 and the width 42 may be sufficient to receive one, two, or any number of cable conductors 36. The height 44 of the cavity 22 may be sufficient to receive at least one cable conductor 36. It is noted here that the height 44 may be measured in a direction generally normal to the surface of the body 12 with splice openings 30. This is because, in use, the splice openings 30 may preferably be in contact with each of the cable conductors 36 and thus side by side placement is preferable over stacking placement of cable conductors 36. As such, the height 44 may preferably be limited to that required to receive one cable conductor 36. However, those of skill in the art will understand and appreciate that multiple surfaces of the crimp connector 10 may include splice openings 30 so as to accommodate multiple cable conductor orientations where each cable conductor 36 is in contact with a splice opening 30. As such, the height 44 is not limited to accommodating a single cable conductor 36.

In one embodiment, the crimp connector 10 may include a splice opening 30 or a series of splice openings 30. The splice openings 30 may extend through the wall 18 of the body 12 leading to the cavity 22. As such, the splice openings 30 may create a splice opening face 46 with a height 48 equal to the thickness 20 of the body wall 18, the splice opening face 46 defining the perimeter of the splice opening 30. The splice openings 30 may be situated in line with each other and may be equally spaced. The splice openings 30 may extend through the body wall 18 substantially perpendicular to the outer and inner surface 14, 16. Alternatively, they may extend through the wall 18 at an angle. In still another embodiment, the splice openings 30 may increase or decrease in size as they pass through the body wall 18. In one embodiment, each splice opening 30 is formed by laser cutting, resulting in a relatively sharp edge at the inner termination of the splice opening 30 where the inner surface 16 of the body 12 intersects with the splice opening face 46.

The splice openings 30 may be any shape. As shown in FIGS. 1 and 2, the splice openings 30 may be in the shape of a slot with a length and a width and may be oriented transverse to the longitudinal axis 28 of the body 12. In the case of a slot type splice opening, the slot may extend across the body 12 and have a length substantially equal to the width 42 of the cavity 22.

In one embodiment, the crimp connector 10 is a segment of pre-drawn tubing. In one embodiment, the body 12 is formed of a metal or alloy material (e.g., platinum-iridium, MP35N, or stainless steel) and has a wall thickness 18 of between approximately 0.004 inch and approximately 0.01 inch. In other embodiments, the crimp connector 10 is formed via other manufacturing processes such as metal injection molding etc.

Figure 3:
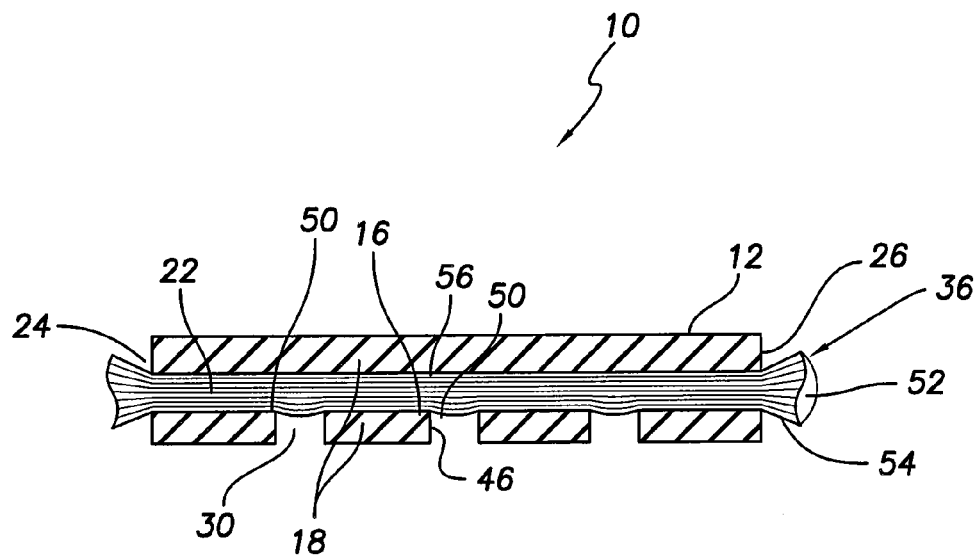
FIG. 3 is a longitudinal cross-sectional view of a crimp connector in post-crimp position in place on a conductor according to certain embodiments.
Figure 4:
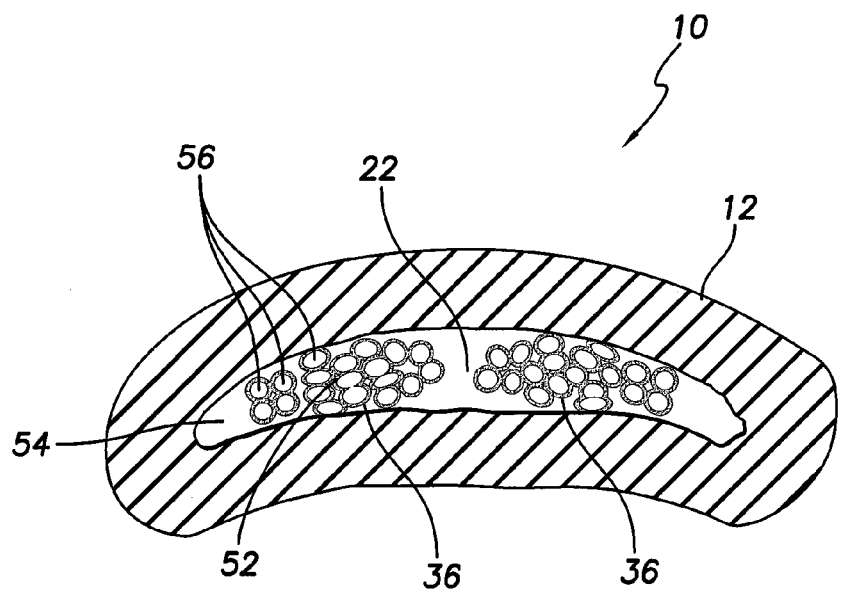
FIG. 4 is a transverse cross-sectional view of a crimp connector in a post-crimp position in place on a conductor according to certain embodiments.

Referring now to FIGS. 3 and 4, the crimp connector 10 may be squeezed, pressed or otherwise caused to crimp the ends of cable conductors 36. This may occur in a crimping anvil and die shaped to achieve a desired resulting crimped shape. Preferably, the squeezing or pressing is directed normal to the surface of the body 12 containing splice openings 30. It is noted that an oblong or oval shaped cross-section may be preferable so as to allow the crimp connector 10 to self-align in the crimping die. FIG. 3 is a longitudinal cross-sectional view of a crimp connector 10 in a post-crimp position in place on a cable conductor 36. The Figure shows the connector body 12, the inner cavity 22, the splice openings 30, and a cable conductor 36. The cable conductor 36 includes a conductive core 52 and an outer insulation jacket 54. As shown, the conductive core 52 may be made up of several strands 56 of smaller wire. The intermittent portions of the wire strands 56 shown are due to the twisted nature of the strands 56 repeatedly crossing the plane of the cross section. The cable conductor 36 may enter the cavity 22 through a proximal end 24 and may extend beyond the distal end 26 as shown. Those skilled in the art will understand and appreciate that the further the cable conductor 36 extends into the cavity 22, the better the connection strength and the electrical conductivity will be.

As shown, the connector 10 has been crimped onto the cable conductor 36 by squeezing or pressing the opposing walls of the connector 10 toward one another in a crimping die, preferably, one of the walls being a wall with splice openings 30. As shown, the insulation 54 of the cable conductor 36 has been pressed into the splice openings 30 due to the forces compressing the cable conductor 36. The sharp edge 50 formed between the splice opening face 46 and the inner surface 16 of the body 12 causes the insulation 54 to be severed and allows for electrical contact between the body 12 and the conductive core 52 of the cable conductor. In the present embodiment, this occurs at each of three splice openings 30 in the connector 10. Moreover, the crimping process has caused the cable conductor 36 to be secured within the connector 10 due to frictional resistance between the cable conductor 36 and the inner surface 16 of the body 12, but also due to bearing type resistance between the bulging portions of the cable conductor 36 and the splice opening face 46 surrounding the splice opening 30.

Referring now to FIG. 4, a transverse cross-sectional view of a crimp connector 10 is shown, wherein the connector 10 is in a post-crimp position and in place on a cable conductor 36. FIG. 4 shows the connector body 12, the inner cavity 22, and two cable conductors 36. The cable conductors 36 shown include a conductive core 52 and an outer insulation jacket 54. As with FIG. 3, the conductive cores 52 may be made up of several strands 56 of smaller wire. As shown, the compressive force of the crimping connector 10 in conjunction with the sharp edge 50 at the splice openings 30 has severed the insulation 54 on the cable conductors 36 allowing electrical contact between the body 12 and at least one strand 56 of each of the conductive cores 52.

Figure 5:
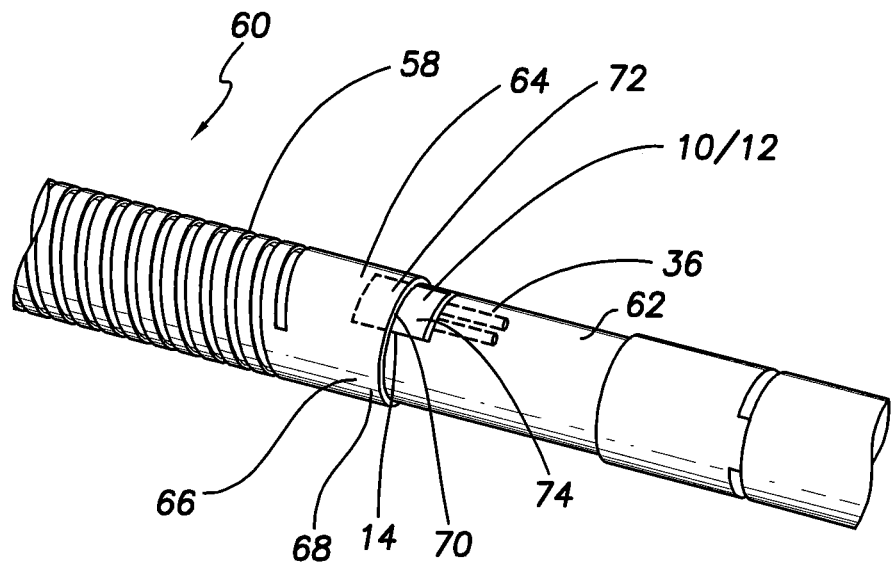
FIG. 5 is an isometric view of a lead with a connector/electrode connection according to certain embodiments.
Figure 6:
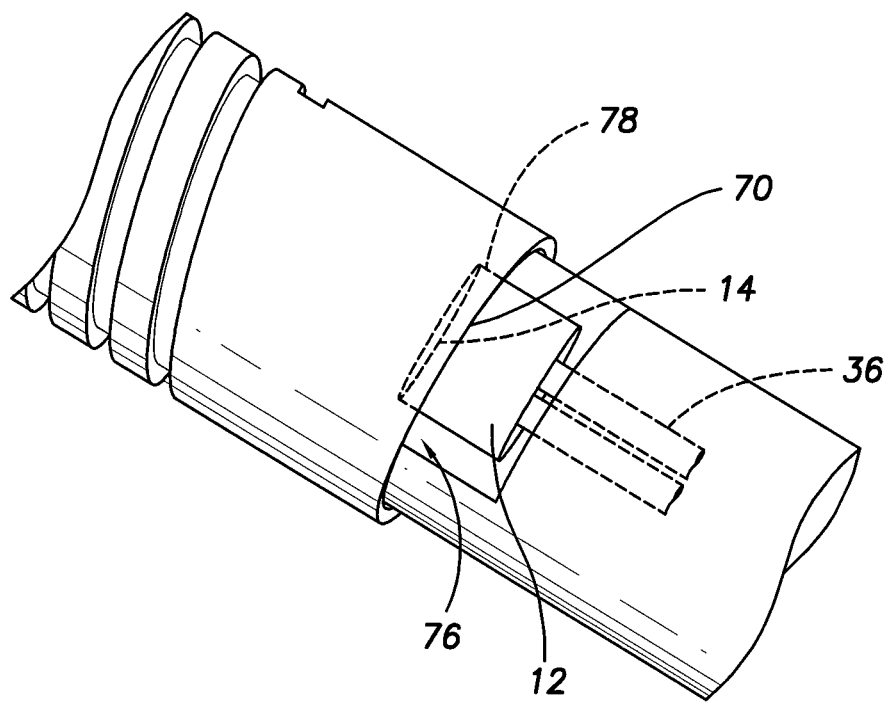
FIG. 6 is an enlarged isometric view of the connector/electrode connection depicted in FIG. 5.
Figure 7:
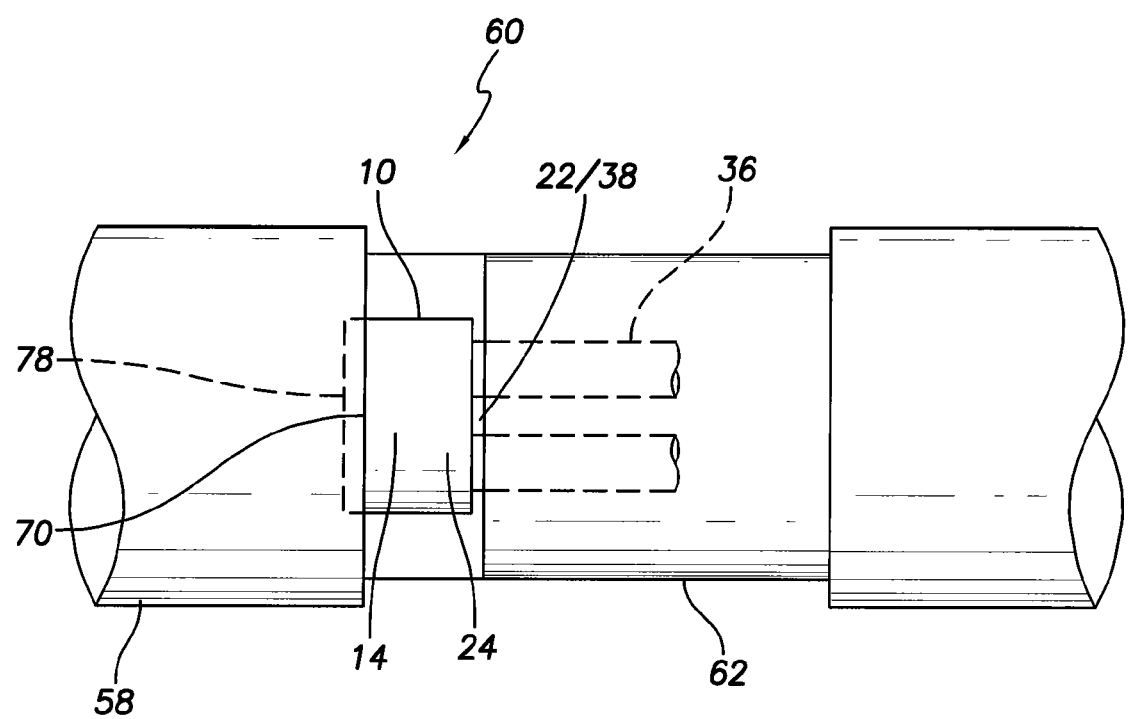
FIG. 7 is an enlarged top view of the connector/electrode connection depicted in FIGS. 5 and 6.

For a discussion of the crimp connector 10 being employed to connect the cable conductors 36 to an electrode 58, reference is made to FIGS. 5-7. FIG. 5 is an isometric view of a lead 60 with a connector 10/electrode 58 connection according to certain embodiments, FIG. 6 is an enlarged isometric view of the connector 10/electrode 58 connection depicted in FIG. 5, and FIG. 7 is an enlarged top view of the connector 10/electrode 58 connection depicted in FIGS. 5 and 6.

As indicated in FIGS. 5-7, in one embodiment, the electrode 58 or electrode assembly 58 extends about the tubular body 62 of the lead 60 and includes a termination ring 64 at a proximal end 66 of the electrode 58. The proximal edge 68 of the termination ring 64 forms a welding face 70 of the electrode assembly 58. A distal portion 72 of the crimp connector 10 may extend underneath the termination ring 64 leaving a proximal portion 74 of the crimp connector 10 extending out of the termination ring 64. As such, the outer surface 14 of the crimp connector 10 may be substantially adjacent to and perpendicular to the welding face 70 of the termination ring 64 allowing for a weld between these two surfaces. It is noted that in this embodiment, the splice openings 30 (not shown) of the crimp connector 10 may be positioned opposite the welded connection to the termination ring 64 to assure a proper welding surface on the body 12 of the crimp connector 10.

As best understood from FIG. 6, the outer surface 14 of the body 12 of the crimp connector 10 may be arcuate allowing it to generally mate with the arcuate shape of the inner surface 76 of the termination ring 64. This may minimize gaps between the outer surface 14 of the crimp connector 10 and the welding face 70 providing for a better welded connection and minimizing weld burn through.

As can further be understood from FIG. 6, in one embodiment, the contour of the immediately adjacent, transversely extending faces 14 and 70 generally match and may be welded together via laser welding in the area 78. In other embodiments, other forms of welding are utilized to join the faces 14, 70, including resistance welding etc. In one embodiment, a series of spot welds (e.g., four spot welds) joins the faces 14, 70 in area 78. In another embodiment, the weld formed in area 78 is generally continuous. Regardless of whether the faces 14, 70 are joined via a series of spot welds or a continuous weld, the welded area 78 defining an edge-to-surface weld is strong due to the relatively extensive length of the welded area 78 made possible by the length over which the faces 14, 70 extend adjacent to each other.

As illustrated in FIGS. 5-7, the cable conductors 36 (shown in phantom) extend through the tubular body 62 of the lead 60 and into the cavity 22 via the proximal opening 38 (see FIGS. 1 and 2) defined by the proximal end 24. Having crimped the cable conductors 36 in the crimp connector 10 and welded or otherwise connected the crimp connector 10 to the electrode 58, the cable conductors 36 may extend through the length of the lead 60 to a controlling device at the other end thus completing the electrical circuit.

Those skilled in the art will understand and appreciate that various modifications may be made to the present disclosure and still be within the scope of the present invention. For example, the body 12 may not be in the shape of a tube, but rather may have a top portion comprising a generally planar or arcuate surface with edges that wrap and hook below the planar surface creating a cavity between each of the wrapped/hooked portions and the bottom surface of the top portion, the wrapped/hooked portions separated by a gap. The cable conductors 36 may be received by the cavities defined by the hooked portion and crimping may cause the wrapped/hooked portions to grasp the cable conductors 36 against the bottom of the top portion. In similar fashion to the tube type body discussed above, this embodiment may have splice openings or slots in the top portion or in the hooked/wrapped portion for severing the insulation and creating electrical conductivity in addition to furthering the connector's ability to grasp the cable conductors 36.

It is noted that the pre-crimp shape of the crimp connector 10 may take on many shapes ranging from completely flat to shapes with pre-formed cavities. In cases where a pre-formed cavity is provided, the crimping process may involve pressing or squeezing the crimp connector 10 to secure the connection to the cable conductor 36. In other cases, the crimping process may actually involve further manipulation of the substrate shape prior to crimping the body to the cable conductor 36. That is, in the case of a flat pre-crimp shape, an edge or edges of the flat body may be folded or rolled around the cable conductor 36 prior to pressing, squeezing, or otherwise crimping the connector 10 onto the cable conductor 36.

In another embodiment, the splice openings 30 may not take the form of the slots discussed above, but may be circular, square, triangular, or any other shape. In some embodiments, the splice openings 30 may not be in line with one another but may be staggered from side to side or more randomly placed. In another embodiment, the splice openings 30 may be in the form of slots, but may extend the full width of the body 12 rather than only the width 42 of the inner cavity 22. Alternatively, the splice openings 30 may stop well short of the width 42 of the inner cavity 22.

In another embodiment, the splice openings 30 may not actually extend all the way through the wall 18 of the body 12. In this embodiment, the splice opening 30 may comprise a recess on the inner surface 16 of the body allowing for the same severing and connection capabilities of the device discussed above, without fully penetrating the body wall 18. In this embodiment, the crimping connector 10 does not need to be oriented so as to have the splice openings 30 directed away from the contact surface of the termination ring 64 of the lead 60 because welding may take place on either surface due the absence of splice openings 30 on the outer surface 14 of the connector 10. Moreover, where the splice openings 30 are located in various positions within the connector 10 (e.g. not all on one side, but on multiple or all sides) the orientation of the connector 10 relative to the crimping die may be more flexible. That is, the crimp connector 10 would not have to be positioned for the crimping die to press on any specific side of the connector 10.

The crimp connector 10 disclosed herein is advantageous for several reasons. First, the crimp connector 10 is bidirectional both with respect to its attachment to the electrode 58 and with respect to its attachment to the cable conductor 36. That is, its symmetry allows for the connector 10 to be rotated so as to exchange positions between its distal end 26 and its proximal end 24. This makes manufacturing easier and also minimizes waste for situations where the connector 10 is inadvertently reversed. Second, the crimp connector 10 does not require removal (e.g., ablation) of cable conductor insulation 54 prior to connecting the crimp connector 10 to the cable conductor 36. This minimizes manufacturing steps for the medical lead 60, reducing costs of production. Third, the crimp connector 10 may be formed from pre-drawn tube subjected to a relatively inexpensive laser cutting process, further reducing costs of production. Fourth, the crimp connector 10 offers improved welding strength and reduced welding difficulty. Accordingly, the crimp connector 10 substantially reduces manufacturing cost associated with connecting cable conductors 36 to the electrodes 58 of implantable cardiac electrotherapy leads 60.

Additionally, the transverse orientation of the splice openings 30 may be advantageous due to the flexibility it provides regarding placement of the cable conductors 36. That is, the cable conductors 36 entering the connector 10 may not need to be placed with any specificity relative to the lateral direction of the connector 10. This is because the breadth of the splice opening 30 may allow for them to be placed anywhere across the width of the cavity 22 and still be in contact with a splice opening 30. Thus, more assurance may be provided that electrical communication will occur between the conductive core 52 of the cable conductor 36 and the sharp edge 50.

Although the present invention has been described with reference to preferred embodiments, persons skilled in the art will recognize that changes may be made in form and detail without departing from the spirit and scope of the invention.

What is claimed is:

1. An implantable cardiac electrotherapy lead comprising:
an electrode on a distal portion of the lead;
a cable conductor extending proximally through the lead from the electrode, the cable conductor having a conductive core and an insulation jacket; and
a crimp connector coupling a distal end of the cable conductor to the electrode, the crimp connector comprising:
a body having a tubular wall with an outer tubular surface, an inner tubular surface, a proximal end, and a distal end;
a cavity; and
at least one splice opening disposed at the tubular wall and having a sharp edge at its intersection with the inner tubular surface, the sharp edge being flush with the inner tubular surface;
wherein the inner tubular surface defines the cavity, the proximal and distal ends respectively define proximal and distal openings leading to the cavity, wherein the at least one splice opening extends from the outer tubular surface to the inner tubular surface and is oriented generally transverse to an axis extending between the proximal and distal openings, and wherein the sharp edge is oriented generally transverse to the axis extending between the proximal and distal openings; and
wherein, in a post-crimp position, opposite ends of the inner tubular surface contact the insulation jacket and the sharp edge penetrates the insulation jacket generally transversely to a longitudinal axis of the insulation jacket and contacts the conductive core to provide electrical communication between the crimp connector and the cable conductor.

2. The lead of claim 1, wherein the body is a segment of pre-drawn tubing.

3. The lead of claim 2, wherein the pre-drawn tubing has an oval cross-section.

4. The lead of claim 1, wherein the at least one splice opening is at least one laser cut splice opening through the tubular wall.

5. The lead of claim 1, wherein the cable conductor is situated in the cavity.

6. The lead of claim 1, wherein the at least one splice opening is at least one slot opening.

7. The lead of claim 6, wherein the at least one slot opening comprises three slot openings.

8. The lead of claim 7, wherein the three slot openings are in line with one another and are equally spaced.

9. The lead of claim 6, wherein the at least one slot opening comprises a first side, a second side, a third side, and a fourth side, wherein the first and second sides oppose each other and are oriented generally transverse to the axis extending between the proximal and distal openings, wherein the third and fourth sides oppose each other and are oriented generally parallel to the axis extending between the proximal and distal openings, and wherein the sharp edge is disposed at the first and second sides.

10. The lead of claim 9, wherein the lengths of the first side and the second side are substantially the same, and wherein the lengths of the third side, and the fourth side are substantially the same.

11. The lead of claim 1, wherein in the post-crimp position, the sharp edge remains flush with the inner tubular surface.

12. An implantable cardiac electrotherapy lead comprising:
a tubular body;
an electrode on the tubular body with a termination ring, the termination ring having an arcuate inner surface and a proximal edge;
a cable conductor including an end, the cable conductor having a conductive core and an insulation jacket; and
a crimp connector with an inner surface defining a cavity and an arcuate outer surface, the crimp connector comprising:
a body having a tubular wall with an outer tubular surface, an inner tubular surface, a proximal end, and a distal end;
a cavity; and
at least one splice opening disposed at the tubular wall and having a sharp edge at its intersection with the inner tubular surface, the sharp edge being flush with the inner tubular surface;
wherein the inner tubular surface defines the cavity, the proximal and distal ends respectively define proximal and distal openings leading to the cavity, wherein the at least one splice opening extends from the outer tubular surface to the inner tubular surface and is oriented generally transverse to an axis extending between the proximal and distal openings, and wherein the sharp edge is oriented generally transverse to the axis extending between the proximal and distal openings; and wherein, in a post-crimp position, opposite ends of the inner tubular surface contact the insulation jacket and the sharp edge penetrates the insulation jacket generally transversely to a longitudinal axis of the insulation jacket and contacts the conductive core to provide electrical communication between the crimp connector and the cable conductor.

wherein the arcuate outer surface of the crimp connector nests substantially continuously against the arcuate inner surface of the termination ring, the crimp connector couples the cable conductor to the termination ring, and the crimp connector includes a segment of a pre-drawn tubing.

13. The lead of claim 12, wherein the at least one splice opening is at least one laser cut splice opening having a sharp edge at its intersection with the inner surface of the crimp connector.

14. The lead of claim 13, wherein the end of the cable conductor is situated in the cavity.

15. The lead of claim 12, wherein the outer surface of the crimp connector is fixedly attached to the proximal edge of the termination ring.

16. The lead of claim 12, wherein the outer surface of the crimp connector is welded to the proximal edge of the termination ring.

* * * * *